United States Patent [19]

Brandes

[11] Patent Number: 5,279,148
[45] Date of Patent: Jan. 18, 1994

[54] METHOD AND APPARATUS FOR DETECTING AND LOCATING LEAKS AND LOOSE COUPLINGS IN CONDUITS FOR LIQUIDS

[76] Inventor: Bernd Brandes, Mühlengrund 4, W-2325 Grebin, Fed. Rep. of Germany

[21] Appl. No.: 786,048

[22] Filed: Oct. 31, 1991

[51] Int. Cl.$^5$ ............................................. G01M 3/40
[52] U.S. Cl. .................................. 73/40.5 R; 324/526
[58] Field of Search .......... 73/40.5 R; 324/525, 526; 340/605

[56] References Cited

FOREIGN PATENT DOCUMENTS

| | | | |
|---|---|---|---|
| 2261308 | 9/1973 | Fed. Rep. of Germany ... | 73/40.5 R |
| 33581 | 3/1977 | Japan ................................ | 73/40.5 R |
| 1-35375 | 11/1978 | Japan ................................ | 73/40.5 R |
| 79229 | 6/1981 | Japan ................................ | 73/40.5 R |
| 51619 | 3/1982 | Japan ................................ | 73/40.5 R |
| 1455415 | 11/1976 | United Kingdom ............ | 73/40.5 R |

Primary Examiner—Hezron E. Williams
Assistant Examiner—Joseph W. Roskos
Attorney, Agent, or Firm—Spencer, Frank & Schneider

[57] ABSTRACT

A method of determining leaks and loose couplings in a pipe system which transfers liquid medium, and an apparatus for implementing that method. The pipe system includes a conduit having a beginning, an end, an inner pipe which carries the liquid medium and an outer pipe which surrounds the inner pipe. The conduit has a filler material which fills in an annular space between the inner and outer pipes. The leaks and loose couplings are detected and isolated by measuring only resistances of the filler material between the beginning of the conduit and ground yielding a first resistance value, between the end of the conduit and ground obtaining a second resistance value, and finally between the beginning of the conduit and the end of the conduit obtaining a third resistance value. The defect is then detected and located in the conduit using the first, second and third resistance values.

11 Claims, 2 Drawing Sheets

METHOD AND APPARATUS FOR DETECTING AND LOCATING LEAKS AND LOOSE COUPLINGS IN CONDUITS FOR LIQUIDS

BACKGROUND OF THE INVENTION

1. Field of the Invention

The present invention relates generally to a method and apparatus of detecting and locating leaks in a pipe system, and in particular, to a method of determining and locating leaks in conduits having an inner pipe carrying a liquid, an outer pipe surrounding the inner pipe and a filler material in an annular space between the inner and outer pipes.

2. Description of the Related Art

Conduits are, for safety reasons, composed of an inner pipe carrying a liquid medium and an outer pipe enclosing the inner pipe. In practice, it is necessary to detect a leak in one of the walls as quickly and easily as possible and to determine the location of that leak. When a leak occurs, either the liquid medium inside the inner pipe or water present on the outside of the outer pipe enters into the space between the inner and outer pipes.

In older pipe systems, it has been difficult to detect and locate defects resulting in leaks, because perspiration tended to form in air spaces between the pipes due to changes in temperature (breathing). Hence, when conventional type sensor cables were introduced, they often reported defects, whether or not a leak was actually present. For example, in sewer systems, the space between sewer pipes is often filled with foamed concrete for reasons of stability. This concrete is wet by nature and consequently unsuitable for leak monitoring. If a leak occurs within such a conduit, the filler material becomes wetter at the location of the leak in the space between the pipes. However, this increased wetness cannot be detected quickly at the accessible ends of the pipes either optically or by measuring technology methods.

In newer installations, the pipes are stabilized relative to one another, that is, the space between the pipes is filled with foam which keeps that space dry. However, if the foam has closed pores this can greatly delay detection of a leak. Also, if the foam has open pores, the damage spreads, making it harder to locate the leak.

SUMMARY OF THE INVENTION

Therefore, it is an object of the present invention to provide a simple, universally applicable method for detection and location of defects (e.g., leaks and loose couplings) in a pipe system.

This is accomplished according to the invention by a method of detecting leaks and loose couplings in a pipe system which transfers liquid media, the pipe system including conduits each having a beginning, an end, an inner pipe carrying the liquid medium and an outer pipe surrounding the inner pipe and defining an annular space between the inner and outer pipes, comprising providing a filler material in the annular space between the inner and outer pipes; measuring ohmic resistances of the filler material between the beginning of the conduit and ground to obtain a first resistance value, between the end of the conduit and ground to obtain a second resistance value, and between the beginning of the conduit and the end of the conduit to obtain a third resistance value; and determining a location of a defect in accordance with the first, second and third resistance values.

An additional feature of the method includes the step of adding electrically conductive, preferably non-corrosive, material to the filler material in order to enhance the electrical conductivity of the filler material.

According to another aspect of the invention there is provided an apparatus for implementing the above method, including: first and second measuring probes each having first and second ends, the measuring probes each including a conductor surrounded by insulation with the first end of each measuring probe having the insulation removed, the first end of the first measuring probe being inserted into the filler material at the beginning of the conduit and the first end of the second measuring probe being inserted into the filler material at the end of the conduit; and an electrical measuring device connected to the second end of the first and second probes for determining the first, second and third resistance values.

An additional feature of the apparatus includes providing a first pair of the measuring probes at the beginning of the conduit and a second pair of the measuring probes at the end of the conduit, the first ends of the conductors of the first pair of probes being arranged mutually offset from each other in the filler material at the beginning of the conduit, and the first ends of the conductors of the second pair of probes being arranged mutually offset from each other in the filler material at the end of the conduit.

The inner and outer pipes, provided as a safety measure, often permit quick and irreversible spreading of a liquid in the case of damage. Filling the annular space which, in the past, has prevented location of defects, is now utilized together with its characteristics (plugging of the annular space, inclusion of construction moisture), which in the past had been considered to have an adverse effect, to limit damage, allow extensive monitoring and easily locate defects.

In accordance with the invention, the insulation resistance of the filler material against the ground (constituted by the medium in the interior and, for example, by moisture in the ground on the exterior), and the point of greatest conductivity relative to the ground (without the presence of a defect source) are defined as the normal state, independently of their respective absolute values. These values are then monitored. A deviation from these values is recorded as the basis for the location of a defect and for necessary reaction. Moisture in the filler material in the annular space, which in the past has been avoided whenever possible, is intentionally accepted and utilized in an advantageous manner for the formation of a measurable conductivity of the filler material.

According to a further aspect of the invention, the conductivity of the filler material is intentionally increased with the addition of an electrically conductive material and is thus stabilized in a calculatable manner. Preferably, a sudden deviation of the measured values (which have been constant over a longer period of time) is evaluated as a criterion for the presence of a defect. By comparing the measured values it is additionally possible to determine the location of a defect along the conduit with sufficient accuracy.

Preferably, the measuring result is transmitted in each case from the end of the conduit to the beginning of the conduit by means of a measuring line. At the beginning of the conduit, the measuring results from the beginning of the conduit and from the end of the conduit are then fed to a measuring and evaluation circuit which provides information as to whether and where in the conduit a defect exists.

According to a further feature of the invention, the measuring results from two essentially similar conduits are compared. Without the occurrence of a defect and under the same environmental conditions, these results are approximately identical. When a deviation between these normally identical or similar measuring results occurs, a conclusion can be drawn as to the presence of a defect. Generally, the defect lies in the section of the conduit which indicates a lower insulation resistance of the filler material to ground.

The invention will now be described in greater detail with reference to the figures.

DETAILED DESCRIPTION OF THE PREFERRED EMBODIMENTS

Figure 1:
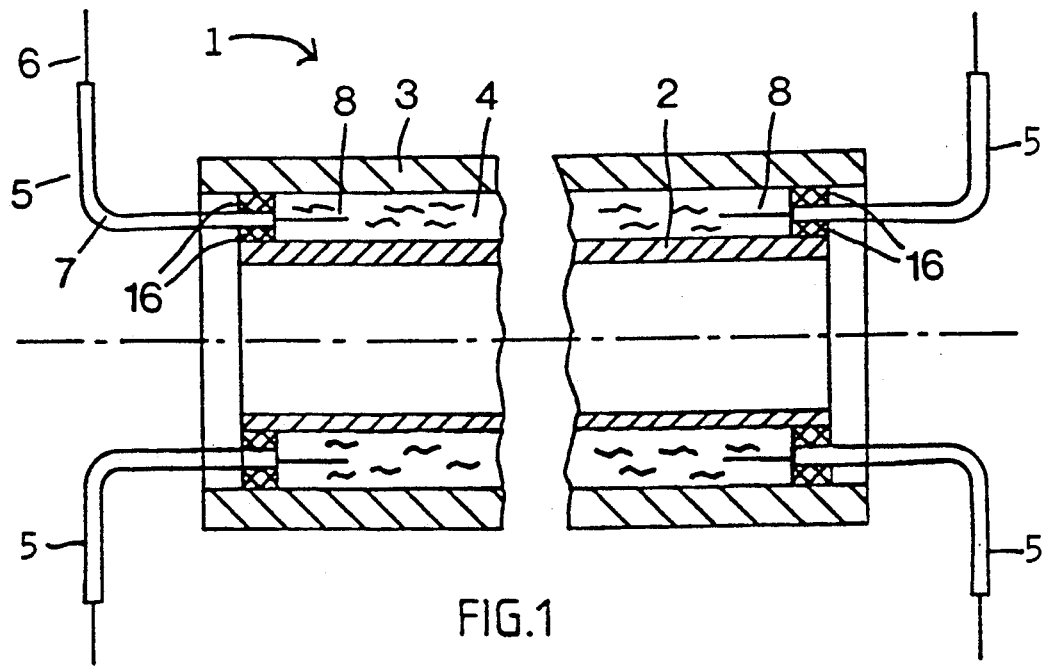
FIG. 1 is a cross sectional view of a conduit including a measuring device according to the invention.

In FIG. 1, a conduit 1 is composed of an interior or inner pipe 2 for transporting a liquid medium and an exterior or outer pipe 3. Filler material 4 is disposed in an annular space between interior pipe 2 and exterior pipe 3. Two probes 5 are inserted at the beginning of conduit 1 and two probes 5 are inserted at the end of conduit 1 at diametrically opposite locations. Probes 5 are composed of a conductor 6 surrounded by insulation 7. An end 8 of probe 5 has insulation 7 removed so that it is in contact with filler material 4. The ends of probes 5 remote from conduit 1 are each connected to a measuring device (not shown in FIG. 1). Filler material 4 at the ends of conduit 1 is insulated from ground by an electrically insulating layer 16, thereby eliminating any undesirable grounding.

Figure 2:
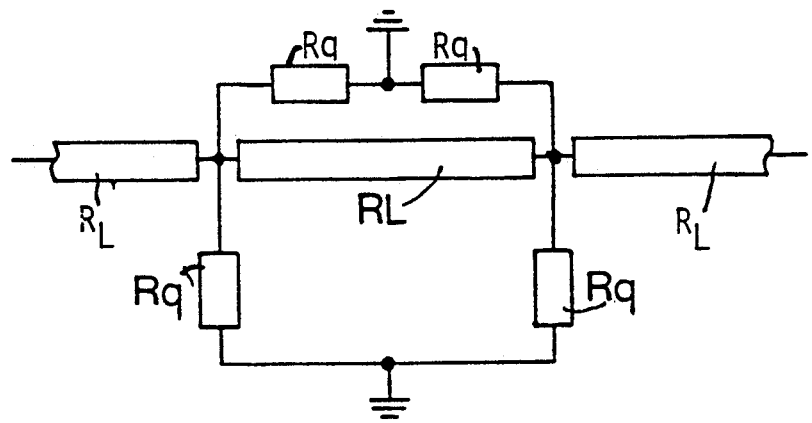
FIGS. 2 and 3 are equivalent circuit diagrams for the electrical characteristics of the conduit.

FIG. 2 shows in a simplified illustration the ohmic longitudinal resistances RL for filler material 4 and the transverse resistances Rq which are distributed over the length of conduit 1 and constitute the insulation resistance of the filler material to ground. Each conduit has a so-called insulation focal point or a defect focal point, which can be thought of as corresponding to a "center of conductivity" point for filler material 4 which has a distributed conductivity in much the same way as a center of gravity point for filler material 4 which has a distributed mass. In a conduit without defects, this focal point lies at 50% of the length of the conduit, since in that case the leakage resistance Rq is distributed uniformly over the entire length of the conduit.

Figure 3:
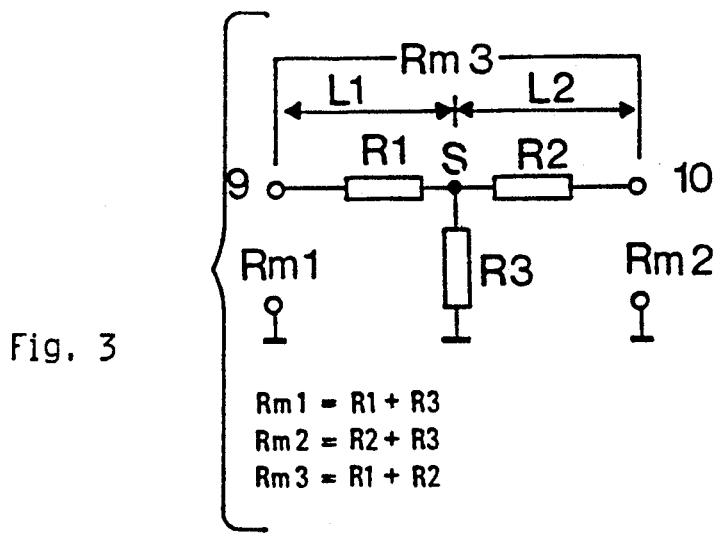

FIG. 3 shows the electrical equivalent circuit diagram in a simplified manner. $R_1$, $R_2$ constitute the longitudinal resistances of filler material 4, while R3 constitutes the resistance from the defect focal point S to ground. By measuring the input resistance Rm1 at terminal 9 with no load on output terminal 10, the value Rm1 = R1 + R3 can be determined. Correspondingly, the value Rm2 = R2 + R3 can be determined by measuring the input resistance at terminal 10 with terminal 9 open. Finally, by measuring the resistance between terminals 9 and 10, it is possible to determine the value Rm3 = R1 + R2 provided inputs 9 and 10 are open circuited with respect to ground. This results in the three illustrated equations with three unknown quantities from which the values for R1, R2, R3 can be calculated separately.

The ratio of R1 to R2, is then used to determine the location of the defect focal point S. In this connection, R1/R2 = L1/L2. This measurement is applicable independently of the absolute values of R1, R2, R3. Increasing the moisture in the annular space between interior pipe 2 and exterior pipe 3 would not falsify the measuring result relative to the location of defect focal point (S). On the other hand, a defect would increase the conductivity toward ground at the location of the defect, that is, resistance R3 would become lower. In addition, other measuring processes known in the cable measuring art, particularly the four-pole measuring process by way of probes 5, are also possible for locating defects.

Figure 4:
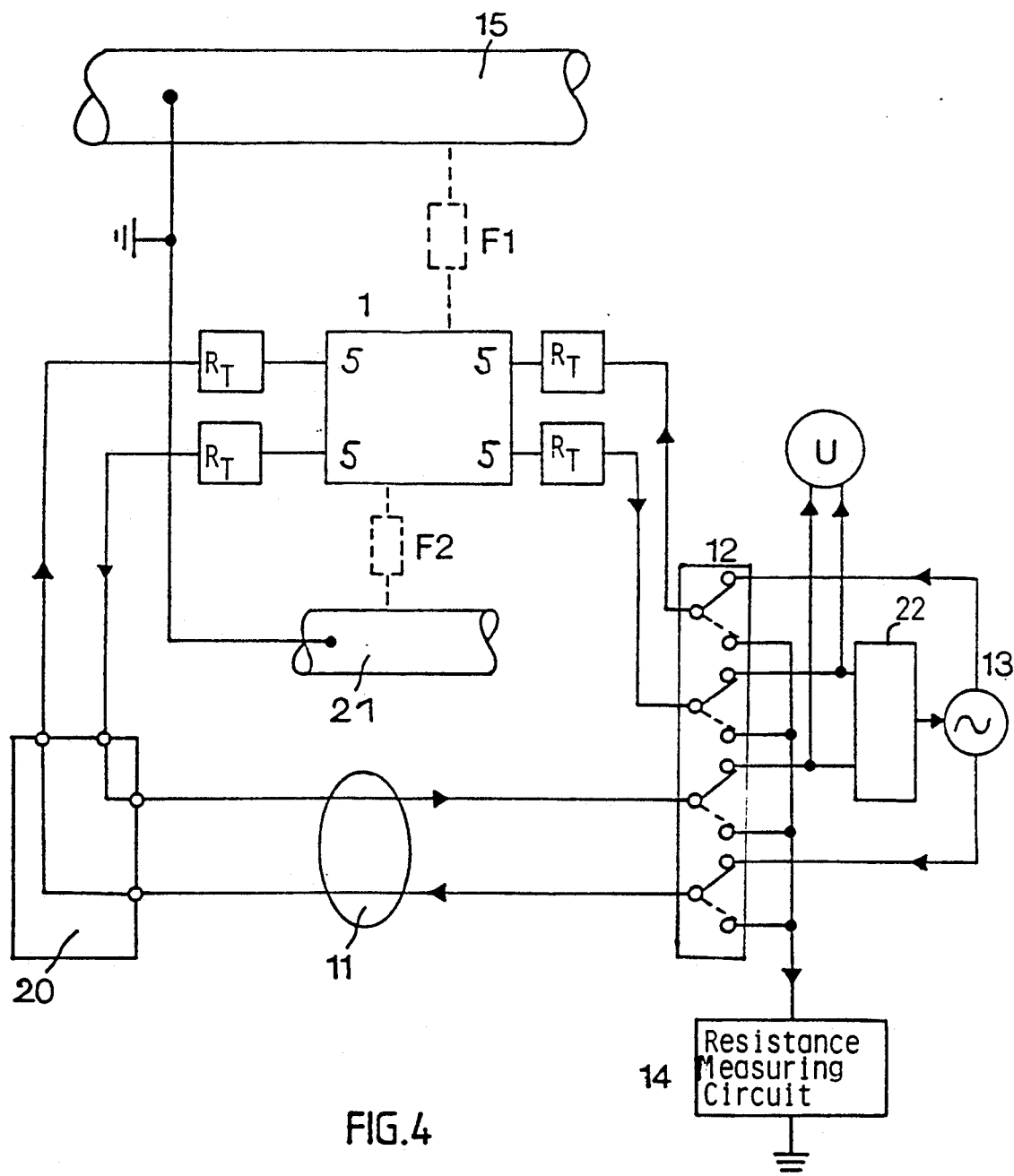
FIG. 4 is an electrical schematic which shows a complete measuring device for a conduit according to the invention.

FIG. 4 is a simplified illustration of conduit 1 to which four probes 5 are connected according to FIG. 1. Each probe 5 has a transfer resistance $R_T$ relative to filler material 4. The measuring results at the left end of conduit 1 are fed to a measuring device 20 and travel from there by way of a measuring line 11 back to the beginning of conduit 1 on the right. A switching unit 12 connects an alternating voltage generator 13 when it is in a position as indicated by solid lines in FIG. 4 with one of the probes 5 at the beginning and end of conduit 1. The voltages supplied to conduit 1 at its beginning and end additionally travel to a controller 22 where they are compared. Controller 22 controls alternating voltage generator 13 in accordance with the results of the comparison, so that alternating voltage generator 13 always outputs a sufficiently large voltage amplitude for controller 22 to make the comparison measurement.

When the switches of switching unit 12 are in the dashed position, the measuring results from the beginning and end of conduit 1 are fed to a resistance measuring circuit 14 where they are evaluated in the previously described manner yielding defect locations F1 and F2. F1 identifies a defect location which may occur between conduit 1 and an outer covering, e.g., a concrete pipe 15, or directly in the ground. F2 identifies the location of a defect which occurs between conduit 1 and a measuring tube 21. Switching unit 12 is operated according to a program so that the individual measurements according to FIG. 3 can be performed successively in time.

The described conduits/pipes may be sewer pipes, fresh water pipes, pipes for liquid chemicals, pipes for transporting water to supply heat to a remote location or for transmitting other liquids. The described defect location F1 may also be disposed between conduit 1 and an outer covering such as, for example, a concrete pipe or directly in the ground. Defect locations F1 and F2 may also be loose grooves in the wall that surrounds filler material 4 in an electrically insulating manner.

According to a further aspect of the invention the resistance values Rm1, Rm2 and Rm3 are measured when no defect is present to define normal resistance values. Subsequently, the occurrence of a defect is determined whenever at least one of the measured resistance values deviates abruptly from a respective one of the normal values.

According to a further aspect of the method of the invention, the measuring results from two essentially similar conduits are compared. Given the same environmental conditions, the results should be approximately identical if there is no defect. When a deviation between the normally identical or similar measuring results occurs, a conclusion can be drawn as to the presence of a defect, with the defect generally being in the section of the conduit which indicates a lower insulation resistance of the filler material to ground.

Obviously, numerous and additional modifications and variations of the present invention are possible in light of the above teachings. It is therefore to be understood that within the scope of the appended claims, the invention may be practiced otherwise than as specifically claimed.

What is claimed is:

1. A method of detecting and locating defects such as leaks and loose couplings in a pipe system which transfers liquid medium, the pipe system including a conduit having a beginning, an end, an inner pipe carrying the liquid medium, an outer pipe surrounding the inner pipe and defining an annular space between the inner and outer pipes, comprising the steps of:

providing a filler material with a definable electrical conductivity in the annular space between the inner and outer pipes;

measuring ohmic resistances of the filler material between the beginning of the conduit and ground to obtain a first resistance value, between the end of the conduit and ground to obtain a second resistance value, and between the beginning of the conduit and the end of the conduit to obtain a third resistance value; and determining a location of a defect using the first, second and third resistance values.

2. A method as defined in claim 1, wherein said providing step includes:

wetting the filler material to enhance the electrical conductivity of the filler material.

3. A method as defined in claim 1, wherein said providing step includes:

adding electrically conductive material to the filler material in order to enhance the electrical conductivity of the filler material.

4. A method as defined in claim 3, wherein said adding step comprises adding electrically conductive, non-corrosive material to the filler material.

5. A method as defined in claim 1, further comprising the step of:

transferring a signal corresponding to the second resistance value by way of a measuring line to the beginning of the conduit.

6. A method as defined in claim 1, wherein said measuring step comprises:

applying an alternating voltage to the beginning and to the end of the conduit; and regulating the amplitude of the alternating voltage to optimize measurement of the resistances values.

7. A method as defined in claim 1, wherein said measuring step includes measuring the first, second and third resistance values when the conduit has no defects to define respective normal resistance values; and said determining step includes identifying an occurrence of a defect whenever at least one of the first, second and third resistance values abruptly changes from a respective one of the normal resistance values.

8. A method as defined in claim 1, wherein the conduit comprises a first conduit section and the pipe system includes an a second conduit section similar in construction to the first conduit section, said method further comprising:

performing said measuring step on the second conduit section, yielding additional first, second and third resistance values; and said determining step includes identifying an occurrence of a defect by detecting a deviation between the first, second and third resistance values as compared with the additional first, second and third resistance values.

9. A method as defined in claim 1, wherein said providing step includes terminating the filler material at the beginning and end of the conduit with electrically insulating material.

10. An apparatus for implementing the method of claim 1, comprising:

first and second measuring probes each having first and second ends, said measuring probes each including a conductor surrounded by insulation with the first end of each said measuring probe having the insulation removed, the first end of said first measuring probe being inserted into the filler material at the beginning of the conduit and the first end of said second measuring probe being inserted into the filler material at the end of the conduit; and an electrical measuring device connected to the second end of said first and second probes for determining the first, second and third resistance values.

11. An apparatus as defined in claim 10, further comprising third and fourth measuring probes constructed similarly to said first and second measuring probes, wherein, the first ends of said first and third measurement probes are arranged mutually offset from each other in the filler material at the beginning of the conduit, and the first ends of said second and fourth measuring probes are arranged mutually offset from each other in the filler material at the end of the conduit.

* * * * *